(12) United States Patent
Chang et al.

(10) Patent No.: US 9,658,164 B2
(45) Date of Patent: May 23, 2017

(54) OPTICAL SENSING CHIP HAVING THREE-DIMENSIONAL NANOSTRUCTURE ARRAY

(71) Applicant: Industrial Technology Research Institute, Hsinchu (TW)

(72) Inventors: Chia-Jung Chang, Yunlin County (TW); Jing-Yuan Lin, New Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 314 days.

(21) Appl. No.: 13/875,305

(22) Filed: May 2, 2013

(65) Prior Publication Data
US 2014/0198376 A1     Jul. 17, 2014

(30) Foreign Application Priority Data

Jan. 14, 2013   (TW) .............................. 102101367 A

(51) Int. Cl.
G01N 21/65    (2006.01)
B82Y 15/00    (2011.01)

(52) U.S. Cl.
CPC ............ G01N 21/658 (2013.01); B82Y 15/00 (2013.01); Y10S 977/92 (2013.01)

(58) Field of Classification Search
CPC ...... G01N 21/658; G01N 21/65; B82Y 15/00; Y10S 977/92; C12Q 2565/632; G01J 3/44
(Continued)

(56) References Cited

U.S. PATENT DOCUMENTS 7,292,334 B1    11/2007   Bratkovski et al.
7,864,313 B2    1/2011    Baumberg et al.
(Continued)

FOREIGN PATENT DOCUMENTS

CN    1659425    8/2005
CN    1938430    3/2007
(Continued)

OTHER PUBLICATIONS

Chia-Jung Chang, Jing-Yuan Lin, and Shang-Chian Su, "High performance Surface Enhanced Raman Scattering optical monitoring in hemodialysis system for quantative analysis", Oct. 28-31, 2012, Sensors, 2012 IEEE, E-ISBN : 978-1-4577-1765-9, Print ISBN:978-1-4577-1766-6.*
(Continued)

Primary Examiner — Kara E Geisel
Assistant Examiner — Violeta A Prieto
(74) Attorney, Agent, or Firm — Jianq Chyun IP Office

(57) ABSTRACT

The present invention relates to an optical sensing chip, which has various applications and may be used repetitively. The optical sensing chip can qualitatively identify different types of molecules and quantitatively analyze small molecules in minute amounts. Regarding a conventional optical sensing chip, an additional sample of known concentration is required as a reference in signal comparison for quantitative determination. In the disclosure, it is unnecessary to add the additional sample of known concentration, but the optical sensing chip itself provides a fixed optical signal that is not varied along with environmental changes to serve as a reference for quantitative determination. In addition, the optical sensing chip also possesses the ability to concentrate or filter sample in real-time.

17 Claims, 4 Drawing Sheets

(58) Field of Classification Search
USPC .......................................................... 356/301
See application file for complete search history.

(56) References Cited

U.S. PATENT DOCUMENTS

| | | | |
|---|---|---|---|
| 8,031,335 | B2 | 10/2011 | Wang et al. |
| 8,129,676 | B2 | 3/2012 | Vestel et al. |
| 2007/0015288 | A1 | 1/2007 | Hulteen et al. |
| 2007/0108068 | A1* | 5/2007 | Suh et al. .................... 205/766 |
| 2010/0248379 | A1 | 9/2010 | Poponin |
| 2011/0046018 | A1 | 2/2011 | Chen et al. |
| 2011/0267610 | A1* | 11/2011 | Hu .................... G01N 21/7746 356/301 |
| 2012/0021918 | A1* | 1/2012 | Bashir et al. .................... 506/2 |
| 2012/0113420 | A1* | 5/2012 | Kuo et al. .................... 356/301 |
| 2012/0119315 | A1* | 5/2012 | Ou et al. .................... 257/431 |
| 2012/0326310 | A1* | 12/2012 | Busnaina et al. ............. 257/746 |
| 2013/0003058 | A1* | 1/2013 | Van Dorpe et al. .......... 356/301 |
| 2013/0027698 | A1* | 1/2013 | Li .................... G01N 21/658 356/301 |
| 2013/0038870 | A1* | 2/2013 | Lin .................... G01N 21/658 356/301 |
| 2013/0157254 | A1* | 6/2013 | Sengupta et al. ................ 435/5 |
| 2014/0186215 | A1* | 7/2014 | Shinta et al. .................... 422/69 |

FOREIGN PATENT DOCUMENTS

| | | |
|---|---|---|
| CN | 101057132 | 10/2007 |
| CN | 102483354 | 5/2012 |
| CN | 102590088 | 7/2012 |
| TW | 200407536 | 5/2004 |
| TW | 200530573 | 9/2005 |
| TW | I325956 | 1/2008 |
| TW | 200921101 | 5/2009 |
| TW | 201140034 | 11/2011 |
| TW | 201224453 | 6/2012 |
| TW | 201226883 | 7/2012 |
| WO | 2012025637 | 3/2012 |
| WO | 2013003709 | 1/2013 |

OTHER PUBLICATIONS

Gang L. Liu et al., "Magnetic Nanocrescents as Controllable Surface-Enhanced Raman Scattering Nanoprobes for Biomolecular Imaging," Advanced Materials vol. 17, Sep. 5, 2005, pp. 2683-2688.

Hui Wang et al., "Quantitative analysis of creatinine in urine by metalized nanostructured parylene," Journal of Biomedical Optics vol. 15, Mar. 23, 2010, pp. 027004.1-027004.5.

Gang L. Liu et al., "Nanowell surface enhanced Raman scattering arrays fabricated by soft-lithography for label-free biomolecular detections in integrated microfluidics," Applied Physics Letters vol. 87, Aug. 11, 2005, pp. 074101.1-074101.3.

Karen E. Shafer-Peltier et al., "Toward a Glucose Biosensor Based on Surface-Enhanced Raman Scattering," J. Am. Chem. Soc vol. 125, Dec. 11, 2002, pp. 588-593.

Hsin-Yi Hsieh et al., "Au-Coated Polystyrene Nanoparticles with High-Aspect-Ratio Nanocorrugations via surface-Carboxylation-Shielded Anisotropic Etching for Significant SERS Signal Enhancement," The Journal of Physical Chemistry C vol. 115, Jul. 19, 2011, pp. 16258-16267.

"Office Action of Taiwan Counterpart Application", issued on Dec. 2, 2014, p. 1-p. 5, in which the listed references were cited.

"Office Action of China Counterpart Application" , issued on Oct. 10, 2015, p. 1-p. 11, in which the listed references were cited.

K Sathiyamoorthy et al., "Surface plasmon enhancement in gold nanoparticles in the presence of an optical gain medium: an analysis", Journal of Physics D: Applied Physics 44(42), Oct. 10, 2011, pp. 1-9.

J. J. Mock et al., "Shape effects in plasmon resonance of individual colloidal silver nanoparticles", Journal of Chemical Physics 116(15), Apr. 15, 2002, pp. 6755-6759.

Xiaoyu Zhang et al., "Electrochemical Tuning of Silver Nanoparticles Fabricated by Nanosphere Lithography", Nano Letters 5(7), Jun. 24, 2005, pp. 1503-1507.

* cited by examiner

OPTICAL SENSING CHIP HAVING THREE-DIMENSIONAL NANOSTRUCTURE ARRAY

CROSS-REFERENCE TO RELATED APPLICATION

This application claims the priority benefit of Taiwan application serial no. 102101367, filed on Jan. 14, 2013. The entirety of the above-mentioned patent application is hereby incorporated by reference herein and made a part of this specification.

BACKGROUND

Technical Field

The disclosure relates to a sensing chip. The disclosure relates to an optical sensing chip.

Related Art

Biosensors currently available in the market are mainly categorized into optical sensing chips depending on a chemical reaction (or color reaction) mechanism or depending on an immunofluorescence labelling mechanism.

The sensor depending on the chemical reaction mechanism always requires molecules having electrochemical activity or uses color-changing molecules to serve as reporters. However, removal of the added reporters after the reaction is difficult, and the reporters may pollute the original analyte sample. Since each reaction may consume a certain proportion of the active reaction surface, it is difficult to perform multiple and persistent detections.

In the immunofluorescence labelling mechanism, fluorescent molecules have to be added, and after the immune response with the fluorescent molecules, chip cleaning has to be performed repeatedly. Although the sensitivity of the immunofluorescence labelling mechanism is good, the immune response requires a longer reaction time and it is unlikely to integrate the immunofluorescence labelling mechanism into a real-time monitoring system during application. As the fluorescent molecules generally have higher biological toxicity, such as the necessity of removing the fluorescent molecules after measurement may arise.

SUMMARY

The disclosure is related to an optical sensing chip of the surface plasmon resonance (SPR) effect, which not only measures very slight changes on a surface of the sensor to achieve high sensitivity, but also implements multiple functions of quantitatively analysis and qualitatively analysis, etc. The sensing chip of the disclosure can also be integrated with flow channel transmission or a signal conversion processing system, etc., to process and identify different types of small molecule environmental or biological samples.

The disclosure provides an optical sensing chip including at least a substrate, an insulating oxide layer, an isolation layer and a three-dimensional nanostructure array. The insulating oxide layer covers the substrate, and the isolation layer covers the substrate and the insulating oxide layer. The isolation layer has at least one opening to expose the three-dimensional nanostructure array located on the insulating oxide layer. The three-dimensional nanostructure array includes a plurality of three-dimensional nanostructures arranged in rows and columns, and any of the three-dimensional nanostructures includes at least one three-dimensional polymer structure and a metal layer conformally covering the three-dimensional polymer structure.

In order to make the aforementioned and other features and advantages of the disclosure comprehensible, several exemplary embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DETAILED DESCRIPTION OF DISCLOSED EMBODIMENTS

Figure 1A:
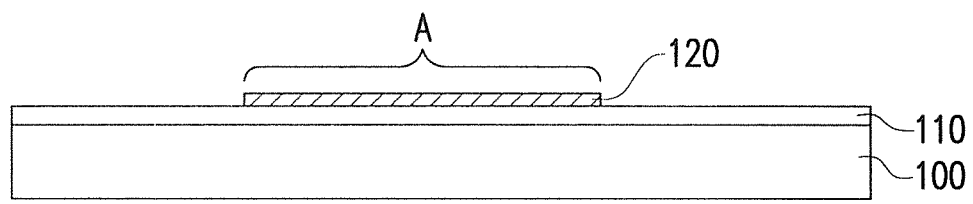
FIGS. 1A-1D are schematic diagrams illustrating a manufacturing process of an optical sensing chip.

The disclosure relates to an optical sensing chip, which can be widely applied to sense various types of small molecules. The so-called small molecules refers to molecules with a molecular weight under 100 kDa, which include chemical molecules, drugs, amino acids, peptides and charged ions, etc. Regarding a biological sample, the measuring mechanism of this sensing chip needs not to employ the immuno-labelling reaction of antibody-antigen.

The disclosure adopts the principles of Raman spectroscopy. Regarding the generation of a Raman characteristic spectrum, owing to the mutual proximity of molecules and metal, the localized surface plasmon resonance (LSPR) effect is generated through the metal surface and the field is localized and enhanced to change the molecule vibrating mode of the molecules to be detected, so as to eventually emit a characteristic fingerprint spectrum having a characteristic Raman wavelength. Such mechanism is generally referred to as surface enhanced Raman scattering (SERS). A main difference between the SERS and the general Raman spectrum is that the SERS is required to have nano metal particles present in the sample to generate the LSPR effect to amplify a Raman signal. The feature of such technique is that different types of molecules can be detected or measured at the same time, and the analyte molecules locating on the surface of the sensor can be measured and determined without using the antibody-antigen immuno-labelling reaction.

One key feature of the main sensing approach of the disclosure is to use a three-dimensional (3D) nanostructure in a suitable size range. When an analyte to be detected comes into a specific rang around the 3D nanostructure, an incident light onto the 3D nanostructure may generate the surface plasmon resonance (SPR) to amplify a local electric field, and such electric field may further influence the Raman signal of the molecules to be detected, so as to amplify the whole Raman signal through the SERS. Compared to the conventional Raman signal, the SERS may amplify the signal with an enhancement factor up to $10^6$-$10^9$. Regarding the SERS (inelastic scattering), for different types of molecules, each type has its own individual characteristic signals. According to this feature that different samples to be detected have different characteristic Raman fingerprint spectrumtra, database of the Raman fingerprint spectrumtra can be built in order to assist the identification of different types of molecules to be detected. Therefore, by measuring specific Raman spectrumtra to identify different biological samples, qualitative analysis of a high accuracy can be achieved.

In the disclosure, as the nano metal particles are fixed on a surface of a sensor used for processing a liquid sample, there is no need to remove the nano metal particles by filtration or other means, which greatly simplifies the operation processing flow of the sensing chip.

In order to increase a contrast between a signal and a background noise, the nano metal structures (particles) are fixed on a surface of a specific sensor in an array. By fixing the nano metal structure array on one plane, the contrast between the signal and the noise can be amplified through the enhanced scattered Raman spectrum.

The structure under the nano metal structure array is composed of two layers of different materials, including a metal electrode layer at the bottom and an insulating oxide layer sandwiched between the nano metal structure array and the metal electrode layer. These two layers have different functions, where the metal electrode layer at the bottom is used to exert an electrostatic force to change an electric property of an electric double layer on the chip surface (i.e. change a zeta potential of the surface). By changing the electric property of the electric double layer on the chip surface, the electric double layer may select ions of different electric properties to reach the surface of the nano metal array. The insulating oxide layer sandwiched in the middle is used to provide a fixed Raman signal that is not changed along with the samples for quantitative use, and each batch of measured data is compared with the fixed Raman signal to determine a real intensity thereof.

FIGS. 1A-1D are schematic diagrams illustrating a manufacturing process of an optical sensing chip.

Referring to FIG. 1A, a substrate 100 is provided. The substrate 100 has an insulating layer 110 thereon and a bottom metal layer 120 located on the insulating layer 110. A low-pressure thermal oxidation method or a low-pressure chemical vapor deposition method (LPCVD) is used to grow the dense insulating layer 110 on the surface of the substrate 100, and the insulating layer 110 is, for example, a silicon dioxide layer. The bottom metal layer 120 is a metal layer, for example, an aluminium layer formed by sputtering and patterned by photolithography and etching. The bottom metal layer 120 is located on the insulating layer 110 and only covers a part of the insulating layer 110. Since the bottom metal layer 120 may be later used as an electrostatic electrode, the bottom metal layer 120 has an electrode pattern A. The substrate 100 is, for example, a silicon substrate or a silicon chip.

Figure 1B:
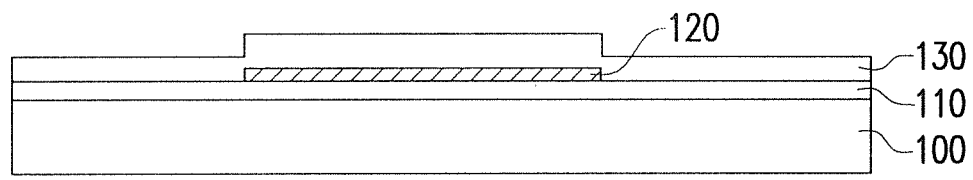

As shown in FIG. 1B, an insulating oxide layer 130 is formed to conformally cover the bottom metal layer 120 and the insulating layer 110. A material of the insulating oxide layer 130 may comprise a metal oxide or silicon oxide. The metal oxide may comprise aluminium oxide. A material of the insulating oxide layer 130 is, for example, metal oxides or silicon oxide, and the insulating oxide layer 130 is formed through a plasma-enhanced chemical vapor deposition (PECVD) method or an atom layer deposition (ALD) method. For example, the insulating oxide layer 130 can be an $Al_2O_3$ layer or a $SiO_2$ layer with a thickness of about 20 nm.

Figure 1C:
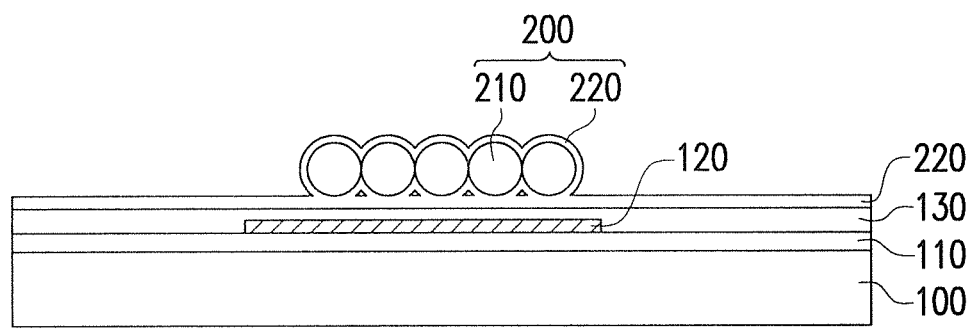

As shown in FIG. 1C, a plurality of three-dimensional (3D) nanostructures 200 is formed on the insulating oxide layer 130. The 3D nanostructures 200 include a plurality of 3D polymer spheres 210 and a metal layer 220 conformally covering at least one of the 3D polymer spheres 210. The 3D polymer spheres 210 are, for example, arranged on the insulating oxide layer 130 through a self-assembly technique driven by surface tension, and the polymer spheres are for example, polystyrene beads with a diameter of about 300 nm. The 3D polymer spheres 210 can be arranged in an array, and an arrangement position and pattern thereof approximately correspond to a position and shape of the electrode pattern A. After the array of the 3D polymer spheres 210 is formed, a thin metal layer 220 is conformally deposited thereon to cover the 3D polymer spheres 210 by a sputtering process, so as to form the 3D nanostructures 200. Moreover, the metal layer 220 also covers the surface of the insulating oxide layer 130 that is not covered by the 3D nanostructures 200. The metal layer 220 is, for example, a gold, silver or copper film with a thickness of about 20-60 nm. The 3D nanostructures 200 respectively have a spherical shape or an oval shape, or has a cone shape (shown in FIG. 2), a columnar shape, a cubic shape, or a cuboid shape, etc., and the 3D nanostructures 200 are arranged in an array, and an arrangement position and a pattern thereof also approximately correspond to a position and shape of the electrode pattern A. The 3D nanostructures 200 mainly uses the metal layer 220 as a surface plasmon resonance (SPR) structure.

Figure 1D:
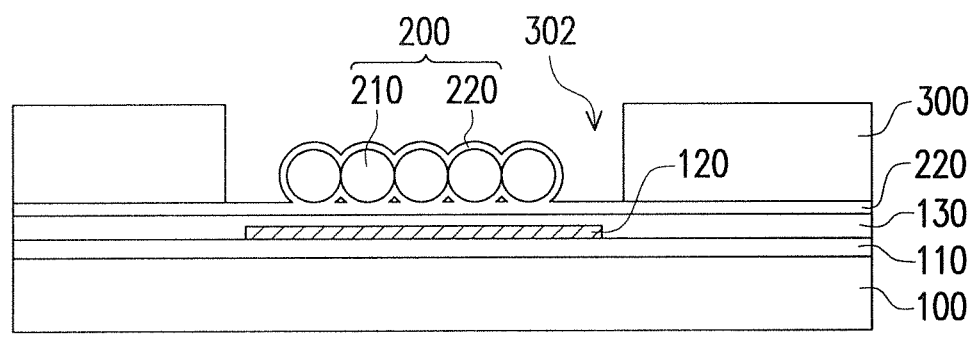

Referring to FIG. 1D, an isolation layer 300 is formed on the metal layer 220. The isolation layer 300 has at least one opening 302, the position, shape and size of the opening 302 also approximately correspond to the electrode pattern A. Namely, the opening 302 does not necessarily expose a full range of the electrode pattern A, but at least exposes the 3D nanostructures 200 arranged in the array and a part of the metal layer 220 conformally covering the insulating oxide layer 130. A material of the isolation layer 300 is, for example, a transparent polymer, for example, polydimethylsiloxane (PDMS). A thickness of the isolation layer 300 is about 1 cm, and the opening 302 may be a round opening with a size of 5 mm.

Figure 2A:
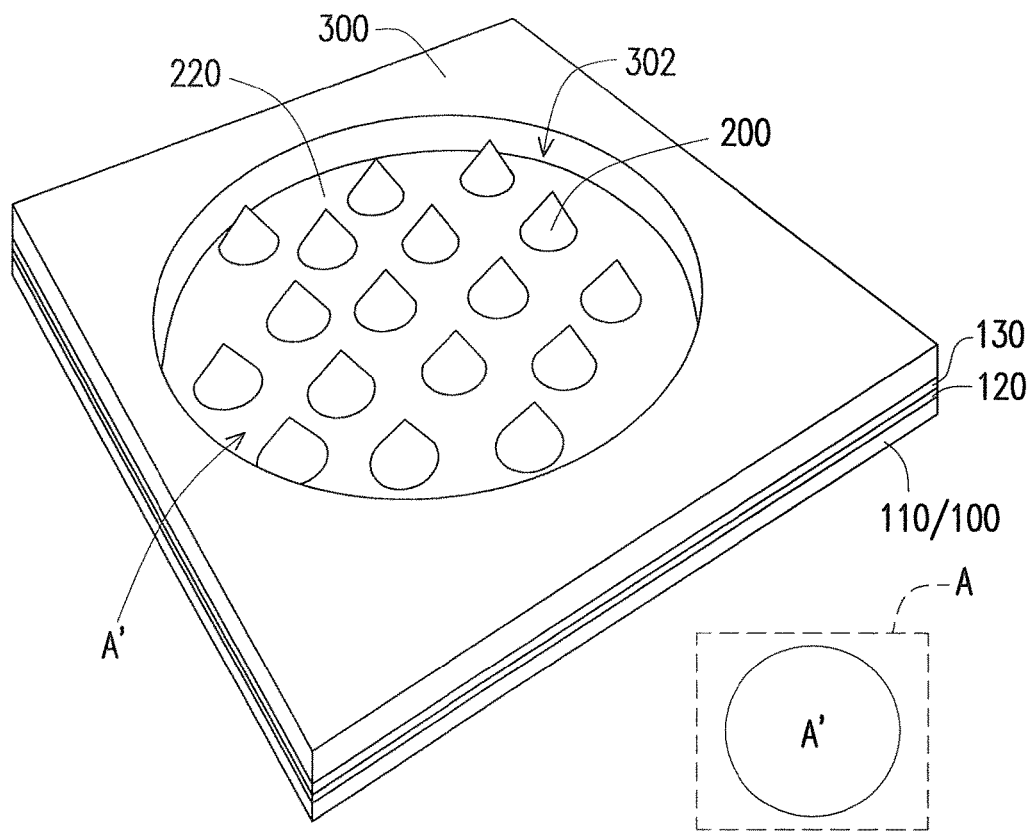
FIG. 2A is a three-dimensional view of an optical sensing chip structure.

FIG. 2A is a schematic three-dimensional view of an optical sensing chip structure. Referring to FIG. 2A, the optical sensing chip structure 20 sequentially includes (from the bottom to the top) the substrate 100, the insulating layer 110 on the substrate 100, the bottom metal layer 120 on the insulating layer 110 and the insulating oxide layer 130 conformally covering the bottom metal layer 120 and the insulating layer 110.

The insulating oxide layer 130 or the substrate 100 can provide a specific and fixed Raman signal. Depending on the material, the Raman signal thereof may have a specific value that remain constant (fixed) regardless the variations of ambient environment. Since the insulating oxide layer 130 or the substrate 100 can provide the specific and fixed Raman signal, the insulating oxide layer 130 or the substrate 100 can be used as a reference signal film layer, and the fixed characteristic Raman signal can be used as a reference for signal comparison to implement the quantitative analysis.

In the present embodiment, the silicon substrate is taken as an example for description purposes, but the substrate is not limited to be the silicon substrate, and the other types of substrates can also be used as long as a film layer structure generated on the substrate after a film plating process can provide a specific and fixed Raman signal for reference. The other types of substrates are, for example, glass, polymer and ceramic substrates.

The bottom metal layer 120 has the electrode pattern A (referring to dot lines at bottom right of FIG. 2A), and the electrode pattern A located between the substrate 100/the insulating layer 110 and the insulating oxide layer 130 serves as an electrostatic manipulation electrode.

The 3D nanostructures 200 are formed on the insulating oxide layer 130 at a position corresponding to the electrode pattern A. The 3D nanostructures 200 include a plurality of 3D polymer spheres 210 and the metal layer 220 conformally covering thereon. The metal layer 220 also covers the surface of the insulating oxide layer 130 that is not covered by the 3D nanostructures 200.

The optical sensing chip structure 20 further includes the isolation layer 300 located on the metal layer 220 and the insulating oxide layer 130. The isolation layer 300 has at least one opening 302. Referring to the bottom left region of FIG. 2, generally, a size of an opening region A' of the opening 302 is smaller than or equal to a size of the electrode pattern A and the position of the opening region A' approximately corresponds to the position of the electrode pattern A. In the present embodiment, the opening has a round shape, though an actual shape thereof can be an arbitrary polygon. Shapes, sizes or positions of the aforementioned electrode pattern, the 3D nanostructure array pattern or the opening pattern can be varied according to an actual chip design, and are not limited to that described in the present embodiment. The 3D nanostructures 200 are exposed by the opening 302 to contact an analyte to be detected, so as to provide the surface enhanced Raman signal.

Due to the thickness of the isolation layer 300, the opening 302 can be regarded as a well or a pit, which is suitable to carry a sample liquid. When the analyte to be detected in the sample liquid comes near the 3D nanostructures 200 within the opening 302, a surface enhanced Raman scattering (SERS) signal is generated by way of the surface plasmon resonance and the SERS signal is used for qualitative analysis and quantitative analysis.

In the disclosure, the isolation layer 300 may have a plurality of the openings 302 arranged in an array, for example, arranged to form a well disc. For example, one unit of the sensing chip may have 16-96 wells (openings), and each well serves as a sensing unit to carry the sample liquid.

Figure 2B:
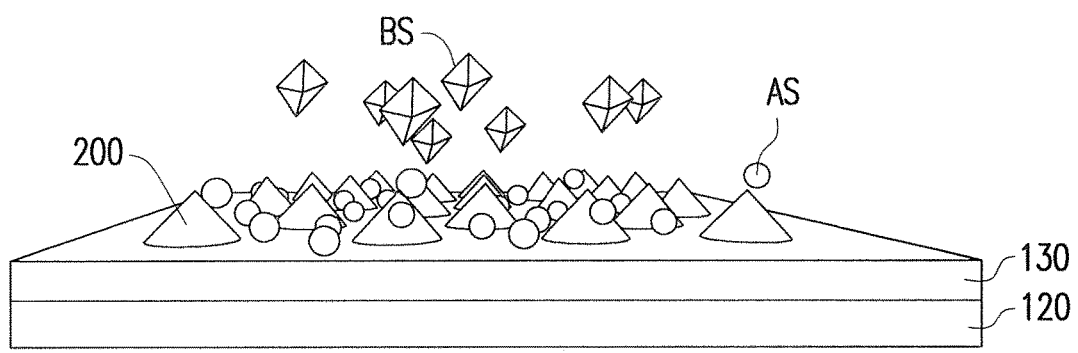
FIG. 2B is a schematic simulation diagram of a sensing mechanism of a sensing chip according to an embodiment of the disclosure.

FIG. 2B is a schematic diagram of a sensing mechanism of a sensing chip according to an embodiment of the disclosure. In FIG. 2B, the conical 3D nanostructures 200 serves as a SPR structure, and when an analyte AS moves into a certain distance range (smaller than or equal to 10 nm) around the 3D nanostructures 200, the incident light on the 3D nanostructure 200 causes the surface plasmon resonance to amplify the whole Raman signal through the surface enhanced Raman scattering (SERS). As shown in FIG. 2B, a bias can be applied to the electrode pattern A on the bottom metal layer 120 that serves as an electrostatic manipulation electrode to change the electric property of the electric double layer on the surface of the chip. In this way, the electric property of the surface electric double layer is changed so as to attract the analyte AS of a different polarity to the surface of the nano metal array (localized aggregation) and repel ions of the same polarity to go away from the surface of the nano metal array (repulsive filtering). Hence, the ions of different electric properties are screened and the undesirable ions are filter out from the surface of the nano metal array.

Namely, the disclosure provides a double layer structure (i.e. the bottom metal layer 120 and the insulating oxide layer 130) capable of controlling the electrostatic double layer, by which the sample concentration reaching the nano metal array sensing chip can be increased (i.e. a concentrated sample) without purifying the sample in advance (for example, without using an ion-filtration membrane or performing drying processing to concentrate the sample), This not only helps the detection of the samples with lower concentrations, but also achieves real-time monitoring by greatly saving the processing time.

Figure 3:
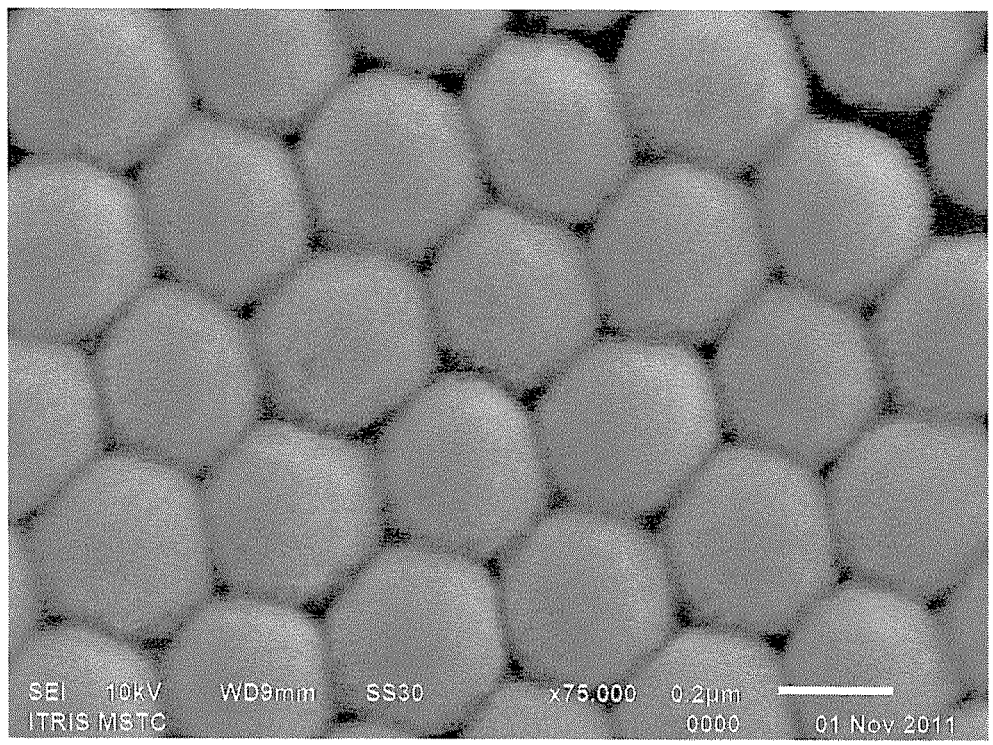
FIG. 3 is a scan-type electron microphotograph of a surface pattern of three-dimensional (3D) nanostructures completed with surface metal sputtering.

FIG. 3 is a scan-type electron microphotograph of a surface pattern of the 3D nanostructures completed with surface metal sputtering. Different to the loosely-arranged 3D nanostructures with a larger pitch of FIG. 2, the 3D nanostructures substantially may be tightly arranged.

In another embodiment of the disclosure, the 3D nanostructures can also be designed as non-fixed 3D structures, and nano particles (with a radius size of about 190 nm) are designed according to the same principle, where the nano particles respectively have a silicon core (with a radius size of 150 nm) which is sequentially wrapped by an insulating oxide layer (with a thickness of 20 nm) and a metal layer (a silver film layer with a thickness of 20 nm), and the nano particles are directly added to the sample, i.e. the 3D nanostructures fixed on the substrate are detached from the substrate.

EXPERIMENT

Figure 4:
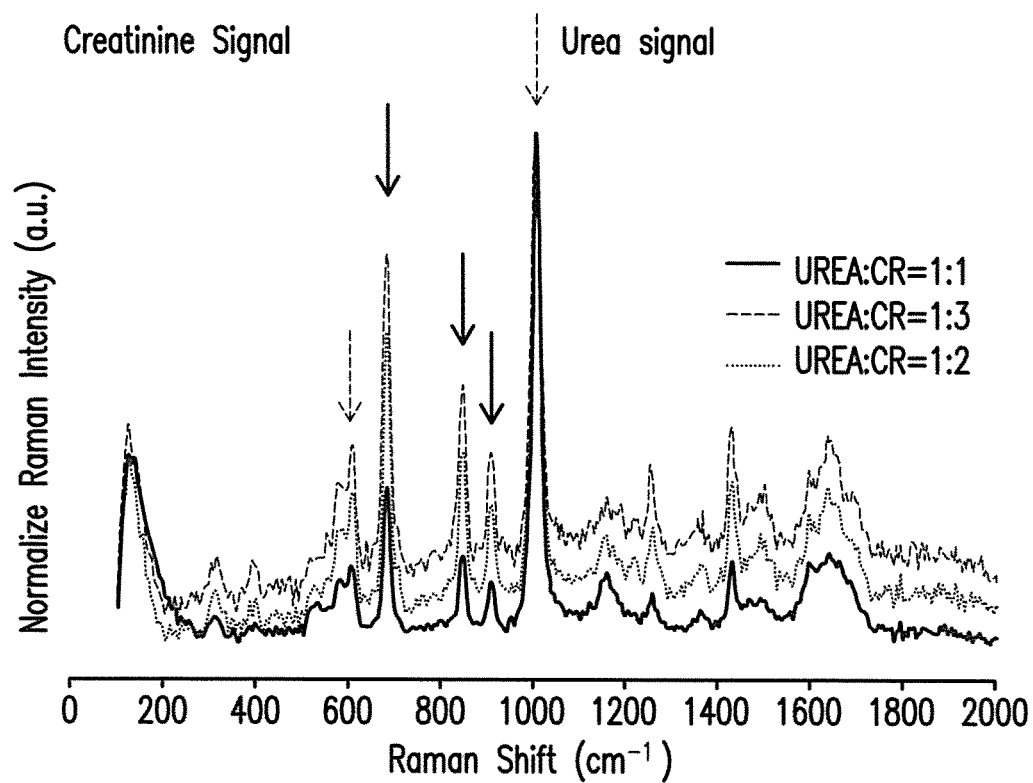
FIG. 4 is a Raman spectrum diagram of a mixed sample according to an embodiment of the disclosure.

The sensing chip of the disclosure may use a QE-65000 Raman spectrometer to implement measurement in collaboration with a frequency doubling NdYAG 532 nm laser used as an excitation source and an optical fiber Raman probe used for reading the corresponding signal. 60 seconds is taken as an integration condition, and 532 nm laser excitation energy is 60 mW. In the disclosure, the sensing chip is used to measure signals of different mixtures under the conditions of different concentration, and prove the test results of the concentrated sample under controlling the surface electric double layer. The analyte sample is a mixture of melamine, urea and creatinine (CR). Different mixtures are first measured on the surface of the enhanced Raman chip. For example, it is determined whether the Raman spectrum can be used to detect a concentration difference by analyzing the signal for the mixtures of the urea and the CR of different concentrations. As shown in FIG. 4, the urea is of a fixed concentration of 10 mM, and the concentration of the CR is variable, which is increased from 10 mM, 20 mM to 30 mM. In FIG. 4, black arrows represent signals of the CR, and red arrows represent characteristic signals of the urea. It is found that the characteristic signals of the urea are not obviously changed, though the signals of the CR are varied along with different concentrations. Therefore, the surface enhanced Raman spectrum has its advantage in qualitative analysis of the mixtures. However, the above method can only identify concentration variation of a certain element, and in order to implement the quantitatively analysis, a fixed signal has to be provided for comparison. For example, in the present embodiment, the urea concentration is a fixed value in the test sample, which can be used for comparison.

Therefore, in the disclosure, the insulating oxide layer having a specific Raman signal is used to server as a reference signal source.

Figure 5:
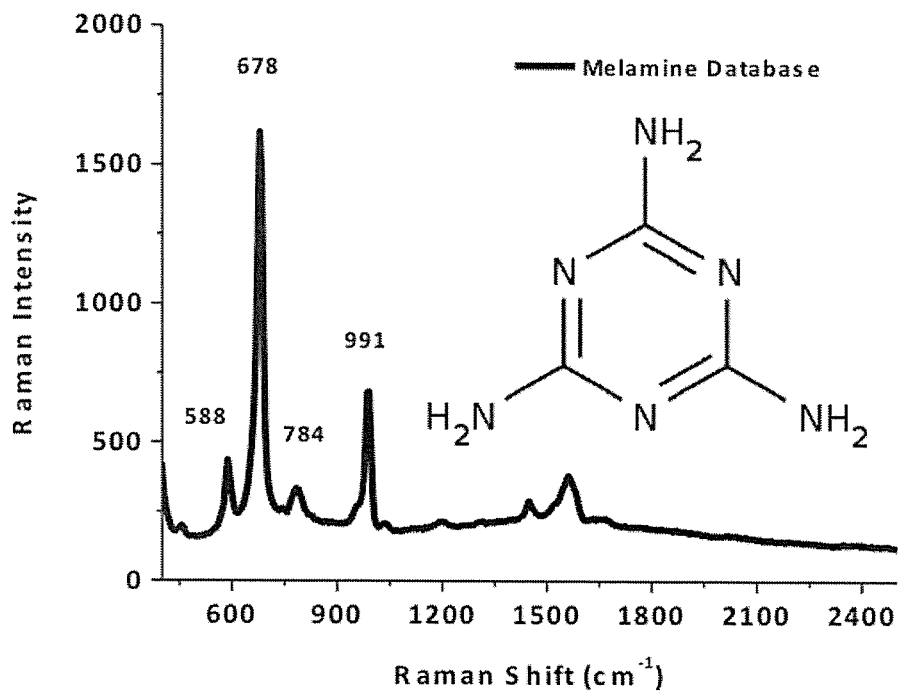
FIG. 5 is a Raman spectrum diagram of a melamine sample according to another embodiment of the disclosure.

In the actual tests of the multi-function chip, silicon dioxide is used as a material of the insulating oxide layer, and a Raman characteristic signal thereof is located on a Raman shift of 525 cm$^{-1}$. Therefore, by comparing the Raman characteristic signal with other signals, the exact concentration of the other signals can be obtained. The melamine plays an important role in the quantitative measurement. First, a characteristic Raman signal of pure melamine is detected to determine whether the measuring result is the melamine. The test spectrum is shown in FIG. 5, according to Raman shift data of pure melamine, it is discovered that the main signals thereof are located at 678 cm$^{-1}$ and 991 cm$^{-1}$.

Figure 6:
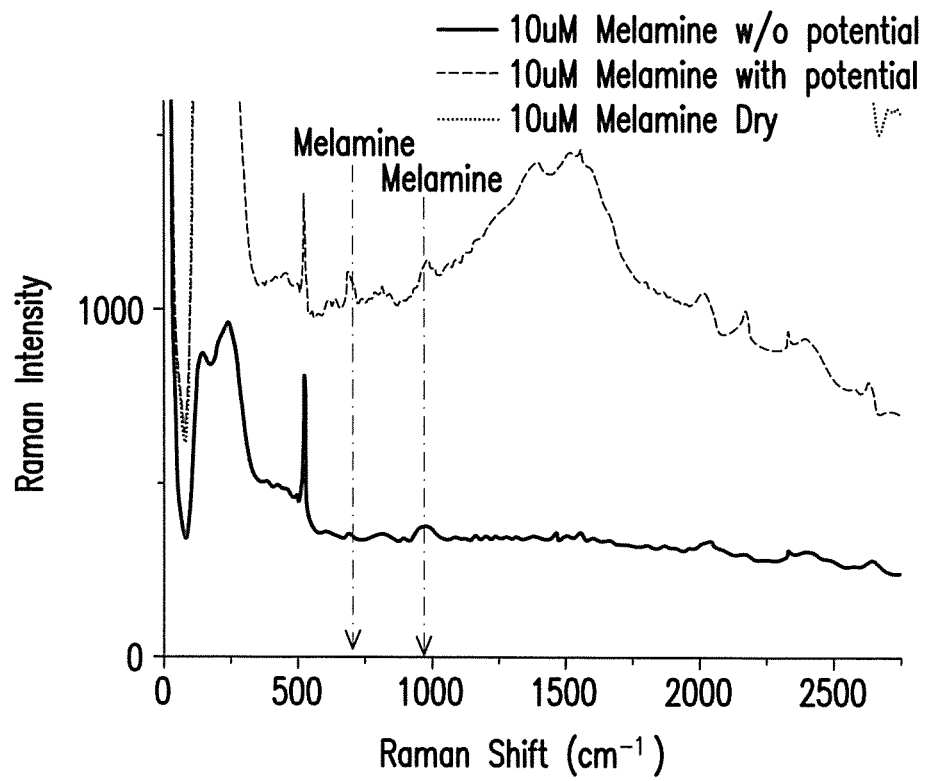
FIG. 6 is a Raman spectrum diagram of a melamine sample according to still another embodiment of the disclosure.

FIG. 6 illustrates test results of the sensing chip of this disclosure for detecting an aqueous solution sample of melamine, and variation caused by applying an electrostatic force is tested. Melamine can be dissolved in water with a weak alkalinity and carry weak positive charges. When the electrostatic force is applied to the chip, it is found that the characteristic signal (dashed line) at 638 cm$^{-1}$ is significantly increased when compared with the situation that none electrostatic force (solid line) is applied to the chip, which represents that the application of the electrostatic force causes a guiding effect for the sample to be measured to reach the nanostructures. By applying the electrostatic force, melamine can be effectively guided to gather at the metal surface of the 3D nanostructures, so as to increase the signal intensity. The reference signal at 525 cm$^{-1}$ is constant, which can provide a reference basis for quantitative measurement.

When the electric property (polarity) of the electric double layer is controlled to be the same polarity with that of the molecules to be measured, a repulsion effect is generated. Conversely, when the electric property of the electric double layer is controlled to be a different polarity with that of the molecules to be measured, a gathering effect is generated. Regarding the low concentration analyte to be measured, the concentration of the analyte to be detected can be as low as 1 ppm. Also, the electrostatic force can be applied to gather the analyte to be detected (concentrate the analyte to be detected) to facilitate the measurement.

At the Raman shift of 525 cm$^{-1}$, a constant signal (provided by silicon dioxide serving as the insulating oxide layer) exists, which is not varied regardless various concentrations of the test samples. All of the measured signal intensities can be compared with the intensity of the reference signal (at 525 cm$^{-1}$) to achieve the quantitative analysis. In the present embodiment, a method of normalization can be used to process the data of the quantitative measurement based on the reference signal.

The optical sensing chip of the disclosure has noticeable structure features, including a stacked structure of metal/insulating oxide layer/nano metal array (from the bottom to the top), and the surface enhanced Raman signal can be provided through the 3D nanostructures of the nano metal array. In the disclosure, the fixed Raman signal layer (i.e. the insulating oxide layer) located on the chip provides the constant reference signal to achieve the quantitative measurement of the analyte.

Moreover, the electrostatic force applied to the chip can be used to implement sample concentration and achieve repulsion of the impurity.

In summary, the testing chip of the Raman optical system has a great application potential, and can be used in testing items such as biomedical pharmacy, environment testing, non-invasive blood glucose testing, food safety rapid detection or microbe rapid screening, etc.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. An optical sensing chip, comprising:
a substrate, wherein the substrate has an insulating layer, at least one insulating oxide layer thereon and an electrode pattern located under the at least one insulating oxide layer, wherein the electrode pattern is directly disposed on the insulating layer and the at least one insulating oxide layer conformally covers a top surface and sidewalls of the electrode pattern;
an isolation layer, covering the substrate and disposed over the at least one insulating oxide layer, wherein the isolation layer has at least one opening; and
a three-dimensional nanostructure array, disposed directly on the at least one insulating oxide layer and over the substrate, wherein a position of the electrode pattern corresponds to a position of the three-dimensional nanostructure array, the three-dimensional nanostructure array is exposed to contact an analyte to be detected, and the three-dimensional nanostructure array comprises a plurality of three-dimensional nanostructures arranged in rows and columns, and any of the plurality of three-dimensional nanostructures comprises at least one three-dimensional polymer structure and a metal layer conformally covering the at least one three-dimensional polymer structure, wherein the metal layer also covers a surface of the at least one insulating oxide layer that is not covered by the plurality of three-dimensional nanostructures,
wherein the plurality of three-dimensional nanostructures serves as surface plasmon resonance structures, while the electrode pattern serves as an electrostatic manipulation electrode.

2. The optical sensing chip as claimed in claim 1, wherein in response to an incident light, the substrate generates at least a specific Raman signal to serve as a reference signal.

3. The optical sensing chip as claimed in claim 2, wherein a material of the at least one insulating oxide layer comprises a metal oxide or silicon oxide, and the substrate is a silicon substrate.

4. The optical sensing chip as claimed in claim 3, wherein the metal oxide comprises aluminium oxide.

5. The optical sensing chip as claimed in claim 1, wherein a thickness of the at least one insulating oxide layer is about 20 nm.

6. The optical sensing chip as claimed in claim 1, wherein the at least one three-dimensional polymer structure is a polystyrene bead with a diameter of 300 nm.

7. The optical sensing chip as claimed in claim 1, wherein the metal layer is a gold, silver or copper film with a thickness ranging from about 20 nm to about 60 nm.

8. The optical sensing chip as claimed in claim 1, wherein a material of the isolation layer comprises a transparent polymer.

9. The optical sensing chip as claimed in claim 8, wherein the transparent polymer comprises polydimethylsiloxane.

10. An optical sensing chip, comprising:
a substrate, wherein the substrate has at least one insulating oxide layer thereon and an electrode pattern underneath the at least one insulating oxide layer, a top surface and sidewalls of the electrode pattern are fully covered by the at least one insulating oxide layer and the electrode pattern is in direct physical contact with the at least one insulating oxide layer;

an isolation layer, covering the substrate and disposed over the at least one insulating oxide layer, wherein the isolation layer has at least one opening, and the electrode pattern and the at least one opening of the isolation layer are located at two opposite surfaces of the at least one insulating oxide layer; and a three-dimensional nanostructure array, disposed directly on the at least one insulating oxide layer and over the substrate, wherein a position of the electrode pattern corresponds to a position of the three-dimensional nanostructure array, the three-dimensional nanostructure array is exposed to contact an analyte to be detected, and the three-dimensional nanostructure array comprises a plurality of three-dimensional nanostructures arranged in rows and columns, and any of the plurality of three-dimensional nanostructures comprises at least one three-dimensional polymer structure and a metal layer conformally covering the at least one three-dimensional polymer structure, wherein the metal layer also covers a surface of the at least one insulating oxide layer that is not covered by the plurality of three-dimensional nanostructures.

11. The optical sensing chip as claimed in claim 10, wherein the at least one three-dimensional polymer structure is a polystyrene bead with a diameter of 300 nm.

12. The optical sensing chip as claimed in claim 10, wherein the metal layer is a gold, silver or copper film with a thickness ranging from about 20 nm to about 60 nm.

13. The optical sensing chip as claimed in claim 10, wherein the at least one opening of the isolation layer is to carry the sample liquid, and a size of the at least one opening is smaller than a size of the electrode pattern.

14. The optical sensing chip as claimed in claim 1, wherein the at least one opening of the isolation layer is to carry the sample liquid, and a size of the at least one opening is smaller than a size of the electrode pattern.

15. An optical sensing chip, comprising:

a substrate, having an insulating layer, at least one insulating oxide layer thereon and an electrode pattern located under the at least one insulating oxide layer, wherein the electrode pattern is directly disposed on the insulating layer and the at least one insulating oxide layer conformally covers a top surface and sidewalls of the electrode pattern;

an isolation layer, covering the substrate and disposed over the at least one insulating oxide layer, wherein the isolation layer has at least one opening;

a plurality of three-dimensional polymer nanostructures, disposed on the at least one insulating oxide layer and positioned within the at least one opening of the isolation layer, wherein the plurality of three-dimensional polymer nanostructures arranged in an array; and a metal layer, conformally covering the plurality of three-dimensional polymer nanostructures and a surface of the at least one insulating oxide layer that is not covered by the plurality of three-dimensional polymer nanostructures.

16. The optical sensing chip as claimed in claim 1, wherein the insulating layer comprises silicon dioxide.

17. The optical sensing chip as claimed in claim 15, wherein the insulating layer comprises silicon dioxide.

* * * * *